United States Patent [19]

Yalvac et al.

[11] Patent Number: 5,310,526
[45] Date of Patent: May 10, 1994

[54] CHEMICAL SENSOR

[75] Inventors: E. Deniz Yalvac; Stephen W. Barr; Selim Yalvac, all of Midland, Mich.

[73] Assignee: The Dow Chemical Company, Midland, Mich.

[21] Appl. No.: 978,566

[22] Filed: Nov. 19, 1992

Related U.S. Application Data

[63] Continuation of Ser. No. 605,808, Oct. 30, 1990, abandoned.

[51] Int. Cl.⁵ .................. G01N 21/00; G01N 21/75; G01N 21/85; C12M 1/34
[52] U.S. Cl. .................. 422/81; 422/82.01; 422/82.06; 435/291; 435/808; 436/165; 436/666; 356/410
[58] Field of Search .............. 422/52, 56, 58, 81, 422/82, 82.01–82.06, 82.08, 82.09; 356/410, 411; 204/409; 436/43, 52, 53, 164, 165, 172, 177, 178, 909, 166, 167, 168, 169; 128/633; 435/291, 807, 808

[56] References Cited

U.S. PATENT DOCUMENTS

| | | | |
|---|---|---|---|
| 3,712,795 | 1/1973 | Hamshere et al. | 436/43 |
| 4,303,419 | 12/1981 | Frank et al. | 422/81 |
| 4,306,877 | 12/1981 | Lübbers | 422/68 |
| 4,331,767 | 5/1982 | Nakajima et al. | 422/82 |
| 4,632,807 | 12/1986 | Marsoner | 422/68 |
| 4,747,687 | 5/1988 | Hoppe et al. | 356/246 |
| 5,039,490 | 8/1991 | Marsoner et al. | 422/82.01 |
| 5,045,919 | 10/1991 | Bryan | 356/246 |
| 5,104,813 | 4/1992 | Besemer et al. | 436/179 |
| 5,116,759 | 5/1992 | Klainer et al. | 422/82.05 |
| 5,157,262 | 10/1992 | Marsoner | 422/82.01 |

Primary Examiner—Robert J. Warden
Assistant Examiner—Christopher Y. Kim
Attorney, Agent, or Firm—Timothy S. Stevens

[57] ABSTRACT

A chemical sensor and method for in-line chemical analysis including a body having a central cavity. The body also has a pair of openings through it to the cavity. A porous plug, such as a ceramic frit, is sealed into each of these openings so that there is a space between the plugs in the cavity. A vent passageway through the body to the cavity is also provided. A pressurized sample is flowed through one porous plug into the cavity while a pressurized reagent is flowed through the other porous plug into the cavity. A component of interest of the sample reacts with a reactive component of the reagent in the cavity to produce a reaction product. The reaction product is analyzed in the cavity by, for example, absorption spectroscopy. As fresh sample and reagent flow into the cavity, the reaction products flow out of the cavity by way of the vent passageway. An ultrasonic vibrator is attached to the body to enhance mixing of the reagent and sample in the cavity

3 Claims, 1 Drawing Sheet

4,310,526

CHEMICAL SENSOR

CROSS-REFERENCE TO RELATED APPLICATION

This is a continuation of application Ser. No. 605,808 filed Oct. 30, 1990, abandoned.

FIELD OF THE INVENTION

The invention is in the field of chemical analysis and more particularly the invention is in the field of chemical sensors suitable for in-line analysis of chemical process streams.

BACKGROUND OF THE INVENTION

Most of the process analytical methods currently in use require sample withdrawal from a chemical process stream and then delivery of this sample via a sample line to a chemical analysis instrument. Often these sample lines, which are expensive to build and maintain, present problems such as delay or difficulty in accessing the more critical points in the process. At times, the sample is pumped and filtered which further complicates operations.

The need for efficient in-line chemical sensors and probes has long been recognized and has led those skilled in this art to design a variety of such systems The diversity of applications, which range from biomedical and environmental monitoring to industrial process control, requires wide variations in physical structure and also performance specifications of these sensors. Most of the fiber optic based sensors described in the literature are based on an immobilized reagent chemistry at the fiber end-face to provide analyte specificity. These sensors suffer from applicability to limited chemistries and probe-to-probe reproducibility. Moreover, problems related to leaching of the reagent, which require continuous calibration and standardization and fragility of the physical structure, inhibit their use for long term in situ process monitoring and control.

SUMMARY OF THE INVENTION

The present invention is a chemical sensor suitable for in-line chemical analysis that solves, to a substantial degree, the above mentioned problems. The present invention comprises a body having a cavity therein. This body has a first aperture therethrough in communication with the cavity and a second aperture therethrough in communication with the cavity and a vent passageway therethrough in communication with the chamber. A first porous member is positioned near the first aperture, the first porous member having at least a first side and a second side, the first side of the first porous member being exposed to the chamber A first sealing means is used for sealing the first porous member to the first aperture so that any fluid exposed to the second side of the first porous member at a pressure greater than the pressure in the chamber will move substantially exclusively through the first porous member into the chamber and then out of the chamber through the vent passageway. A second porous member is positioned near the second aperture, the second porous member having at least a first side and a second side, the first side of the second porous member also being exposed to the chamber A second sealing means is used for sealing the second porous member to the second aperture so that any fluid exposed to the second side of the second porous member at a pressure greater than the pressure in the chamber will move substantially exclusively through the second porous member into the chamber and then out of the chamber through the vent passageway Preferably, an ultrasonic vibrator is also used to vibrate the body so that any fluid contents in the chamber mixes at a faster rate than when the body is not ultrasonically vibrated. The sensor of the present invention can also comprise a light generating and directing means for generating light and directing it into the cavity and a light detecting means for measuring light coming from the cavity so that, for example, the contents of the chamber can be subjected to absorption spectroscopy.

The present invention is also a method for chemical analysis comprising three steps The first step is to move a fluid sample through a first porous member into a reaction space, the sample containing a component of interest The second step is to move a fluid reagent through a second porous member into the reaction space, the fluid reagent containing a reactive component that reacts with the component of interest of the sample to produce a detectable reaction product in the reaction space. The third step is to detect the detectable reaction product in the reaction space by, for example, absorption spectroscopy, emission spectroscopy or by an electrode system. Preferably, the method of the present invention also includes the step of mixing the contents of the reaction space so that the sample and the reagent moved into the reaction space are more rapidly mixed together.

DETAILED DESCRIPTION OF THE INVENTION

Figure 1:
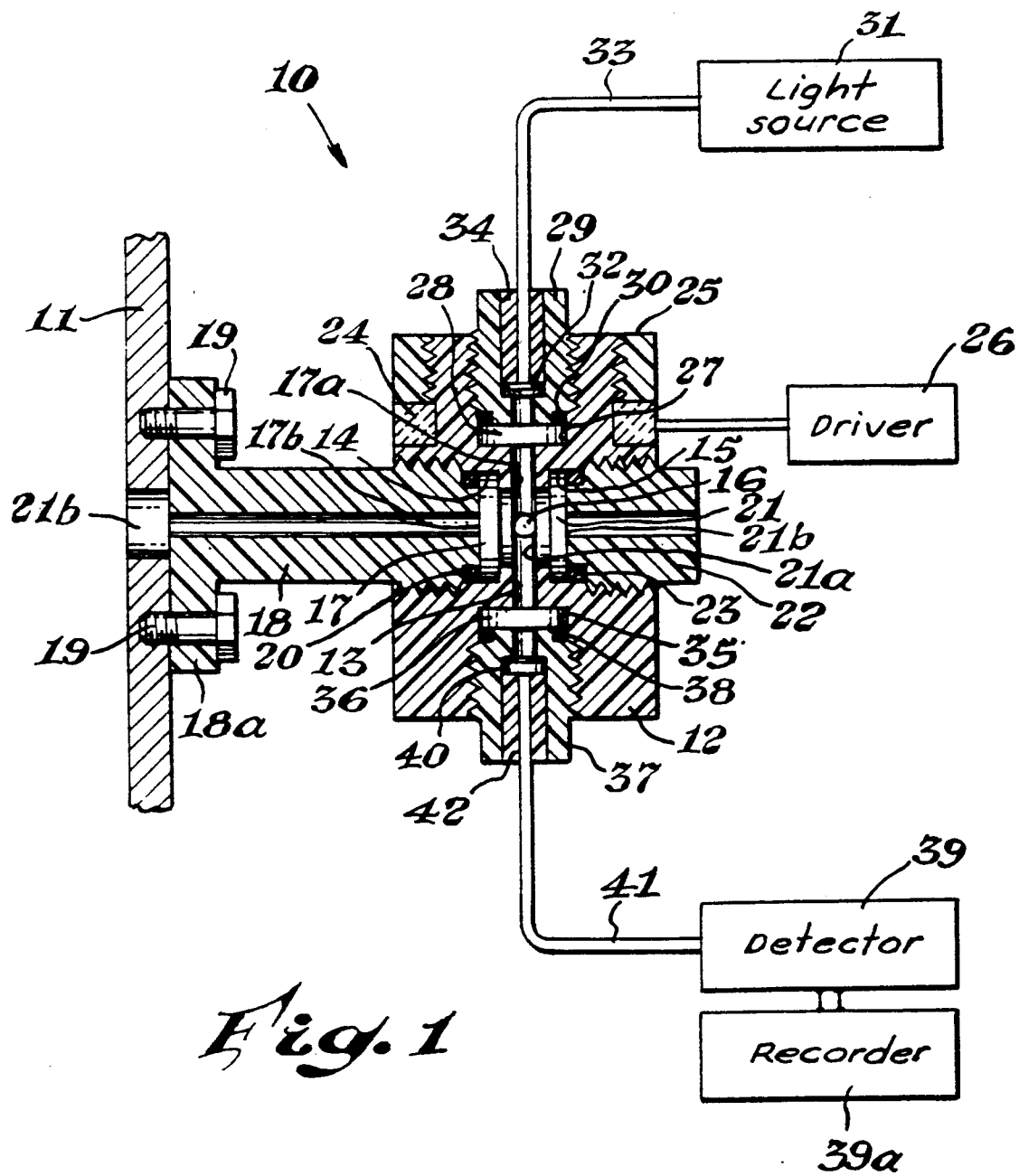
FIG. 1 is a side cross sectional view of a sensor of the present invention attached to the side wall of a chemical reactor.

Referring now to FIG. 1, therein is shown a side cross sectional view of a preferred chemical sensor 10 according to the present invention attached to the side wall 11 of a chemical reactor The sensor 10 has a body 12. The body 12 defines a cavity 13 therein. The body 12 also defines a first aperture 14 therethrough in communication with the cavity 13. The body 12 further defines a second aperture 15 therethrough in communication with the cavity 13. The body 12 also defines a vent passageway 16 therethrough in communication with the cavity 13. A first porous member 17 is positioned in the first aperture 14. The first porous member 17 has a first side 17a and a second side 17b. The first side 17a is exposed to the chamber 13. The first aperture 14 is threaded to accept a bushing 18. The bushing 18 has a flange 18a. Bolts 19 are used to attach the bushing 18 to the side wall 11. In some applications the bushing 18 as shown in FIG. 1 is too long and its mouth too narrow, see the Example below The body 12 can be beneficially inserted directly into a process stream, reactor or other sample source so that the body 12 becomes a probe. It should be understood that the cavity 13 can be miniaturized, e.g., to make a micro-probe, and that the shorter diffusional distances in a miniaturized probe are an advantage in the present invention. An O-ring 20 is used as a first seal to seal the first porous member 17 to the first aperture 14. The reactor wall 11 contains a sample liquid 21b under pressure which is exposed to the second side 17b of the porous member 17 via the mouth of the bushing 18. Therefore, the sample moves through the first porous member 17 into the cavity 13 and then out the vent 16. The O-ring 20 ensures that substantially all of this movement is exclusively through the first porous member 17 and not around it. A second porous member 21 is positioned in the second aperture 15. The second porous member 21 has a first side 21a and a second side 21b. The first side 21a is exposed to the chamber 13. The second aperture 15 is threaded to accept a bushing 22. An O-ring 23 is used as a second seal to seal the second porous member 21 to the second aperture 15. A liquid reagent under pressure is exposed to the second side 21b of the porous member 21 via the mouth of the bushing 22. Therefore the reagent moves through the second porous member 21 into the cavity 13 and then out the vent 16. The O-ring 23 ensures that substantially all of this movement is exclusively through the second porous member 21 and not around it. An O-ring is used as the first and second seal. However, any sealing means could have been used such as a gasket, a sealant, a cement, a brazed joint, a press fit joint and a welded joint. A specific material useful for the porous members 17 and 21 is P-3-C or P-6-C porous alumina available from Coors Ceramics Co., Golden, Colo. However it should be understood that any porous material can be used in the present invention as the porous members, as long as it can be exposed to the sample and reagent. Examples include glass frits, metal frits, ceramic frits, polymer frits, wood plugs, compacted powder packings, such as clay, and porous membranes.

A lead zirconate ceramic ring ultrasonic transducer 24 is attached to the body 12 by a collar 25. The transducer 24 vibrates the body 12 so that any fluid contents in the chamber 13 are mixed at a faster rate than when the body 12 is not ultrasonically vibrated The body 12, the bushing 18 and the bushing 22 are composed of Kynar brand plastic, instead of a metal, because this material better transmits the ultrasonic vibrations and it is chemically resistant to attack from many samples and reagents An ultrasonic square wave voltage generator 26 is used to drive the transducer 24 as is well understood in the art.

The body 12 also defines a third aperture 27 therethrough in communication with the cavity 13. An optical glass window 28 is positioned in the aperture 27. A threaded bushing 29 of Kynar brand plastic and an O-ring 30 retain and seal the window 28 to the body 12. The light source of a Brinkmann PC-1000 fiber optic colorimeter is used as a light source 31. Light from the light source 31 is directed to a lens 32 by a six tenths millimeter diameter $SiO_2$ optical fiber 33. A press fit sleeve 34 of Kynar brand plastic is used to align and retain the end of the fiber 33 that abuts the lens 32. The body 12 also defines a fourth aperture 35 therethrough in communication with the cavity 13. An optical glass window 36 is positioned in the aperture 35. A threaded bushing 37 of Kynar brand plastic and an O-ring 38 retain and seal the window 36 to the body 12. The light measuring portion of a Brinkmann PC-1000 fiber optic colorimeter is used as a detector 39. Light from the cavity 13 is directed through a lens 40 to the detector 39 by a six tenths millimeter diameter $SiO_2$ optical fiber 41. A press fit sleeve 42 of Kynar brand plastic is used to align and retain the end of the fiber 41 that abuts the lens 40. The sensor 10 is thus assembled to perform absorbance spectroscopy on the contents of the cavity 13. A recorder 39a is used to record the signal from the detector 39. The focal length of the lenses 32 and 40 are best selected to collimate and collect the light being introduced into the cavity 13 via the fiber 33 and the lens 32 and collected into the fiber 41 via the lens 40. If the aperture 27 is made to be ninety degrees from the aperture 35 instead of the one hundred and eighty degrees shown, then fluorescence measurements can be made. If the reagent is a chemiluminescent reagent, then the aperture 27, and its associated hardware, can be eliminated. It should be understood that the present invention is not limited to optical methods of analysis of the contents of the cavity 13 and that other means can be used to analyze the contents of the cavity 13 such as electrode systems.

The method embodiment of the present invention can also be understood by reference to FIG. 1. The reactor wall 11 contains a liquid sample under pressure which moves through the first porous member 17 into the cavity 13. A liquid reagent under pressure also moves through the second porous member 21 into the chamber 13. The fluid sample contains a component of interest The reagent contains a reactive component of interest that reacts with the component of interest of the sample to produce a detectable reaction product. The cavity 13 is thus a reaction space for this reaction to take place. The light source 31, the fiber 33, the lens 32, the window 28, the window 36, the lens 40, the fiber 41 and the detector 39 are an absorbance spectroscopy system for detecting the reaction product in the reaction space. Preferably, the contents of the reaction space are mixed so that the sample and the reagent moved into the reaction space are more rapidly co-mingled together This 26. If some type of mixing such as this is not provided, then diffusion is the means for co-mingling the sample and the reagent in the reaction space. In this event, the sensor 10 can take a longer time to respond to a change in the concentration of the component of interest in the sample and the sensitivity of the sensor can be reduced

EXAMPLE

The system of FIG. 1 is assembled as described above. However, the bushing 18 is made shorter and its mouth made larger so that the contents of the reactor wall 11 can easily flow against the second side 17b of the first porous member 17 so that there is a reduced delay time for the sensor 10. The reactor wall 11 contains an aqueous solution including a varying concentration of calcium ions and this solution is under a pressure of ten pounds per square inch gauge. About fifty microliters of this solution flows through the porous member 17 per minute. A reagent of one tenth percent cresolphthalein complexone in an aqueous solution of one tenth molar sodium borate is introduced into the mouth of the bushing 22 under a pressure of ten pounds per square inch gauge. About fifty microliters of this solution flows through the porous member 21 per minute. The vent passageway 16 is connected to a waste bottle at atmospheric pressure. Cresolphthalein complexone reacts with calcium ions in the presence of a borate buffer to produce a colored reaction product absorbing light at a wavelength of five hundred and forty five nanometers. The Brinkmann colorimeter is set at a wavelength of five hundred and forty five nanometers and the recorder 39a is set to record a ten percent transmittance change per inch of chart paper. The driver 26 is turned on. The recorder 39 shows a varying percent transmittance response over a time seven hours and samples are also manually taken every fifteen minutes over this time. The recorder response is converted into relative calcium ion concentration and a table of this concentration is made with a data point for every fifteen minutes during the seven hour period. The manually withdrawn samples are analyzed for calcium ion concentration and a table of these results is made showing a varying calcium ion concentration of from five to one hundred and twenty five parts per million. The table of results for the manually taken samples trends within ten percent of the table of results from the sensor 10.

What is claimed is:

1. A chemical sensor suitable for in-line chemical analysis, comprising:

(a) a body, the body defining a cavity therein, the body also defining a first aperture therethrough in communication with the cavity, the body further defining at least a second aperture therethrough in communication with the cavity, the body also further defining a vent passageway therethrough in communication with the cavity, the body also defining a third aperture therethrough in communication with the chamber, the body further defining a fourth aperture therethrough in communication with the cavity;

(b) a first porous member positioned near the first aperture, the first porous member having at least a first side and a second side, the first side of the first porous member being exposed to the cavity;

(c) a first sealing means for sealing the first porous member to the first aperture so that any fluid exposed to the second side of the first porous member at a pressure greater than the pressure in the cavity will move substantially exclusively through the first porous member into the cavity and then out of the cavity through the vent passageway;

(d) a second porous member positioned near the second aperture, the second porous member having at least a first side and a second side, the first side of the first porous member also being exposed to the cavity;

(e) a second sealing means for sealing the second porous member to the second aperture so that any fluid exposed to the second side of the second porous member at a pressure greater than the pressure in the cavity will move substantially exclusively through the second porous member into the cavity and then out of the cavity through the vent passageway;

(f) light generating and directing means for generating light and directing light into the cavity via the third aperture, the light generating and directing means being coupled to the body; and (g) light detecting means for measuring light coming from the cavity via the fourth aperture, the light detecting means being coupled to the body.

2. The chemical sensor of claim 1, further comprising:

(f) an ultrasonic vibrating means for ultrasonically vibrating the body so that any fluid contents in the cavity are mixed at a faster rate than when the body is not ultrasonically vibrated, the ultrasonic vibrating means being coupled to the body.

3. The chemical sensor of claim 1 wherein the light generating and directing means comprises at least one optical fiber for directing light into the cavity and wherein the light detecting means comprises at least one optical fiber for directing light from the cavity.

* * * * *